United States Patent [19]

Vandenberk et al.

[11] 4,035,369

[45] July 12, 1977

[54] 1-BENZAZOLYLALKYL-4-SUBSTITUTED-PIPERIDINES

[75] Inventors: Jan Vandenberk, Beerse; Ludo E. J. Kennis, Vosselaar; Marcel J. M. C. Van der Aa, Vosselaar; Albert H. M. Th. Van Heertum, Vosselaar, all of Belgium

[73] Assignee: Janssen Pharmaceutica N.V., Beerse, Belgium

[21] Appl. No.: 713,309

[22] Filed: Aug. 10, 1976

Related U.S. Application Data

[63] Continuation-in-part of Ser. No. 620,727, Oct. 8, 1975, abandoned.

[51] Int. Cl.² ...................................... C07D 401/06

[52] U.S. Cl. ...................... 260/293.6; 260/293.57; 260/293.58; 260/293.67; 260/293.79; 260/293.8; 260/304 R; 260/307 C; 260/309.2; 260/573; 260/646; 260/240 D; 424/267

[58] Field of Search ................. 260/293.57, 293.58, 260/293.6, 293.67, 293.79, 240 D

[56] References Cited

FOREIGN PATENT DOCUMENTS

| 659,364 | 8/1965 | Belgium |
| 1,573,739 | 7/1969 | France |

*Primary Examiner*—Cecilia M. S. Jaisle
*Attorney, Agent, or Firm*—Salvatore R. Conte

[57] ABSTRACT

Compounds of the class of 1-(benzazolyalkyl)piperidine derivatives, useful as neuroleptic agents.

7 Claims, No Drawings

1-BENZAZOLYLALKYL-4-SUBSTITUTED-PIPERIDINES

CROSS-REFERENCE TO RELATED APPLICATIONS

This is a continuation-in-part of our copending application Ser. No. 620,727, filed Oct. 8, 1975 now abandoned.

BACKGROUND OF THE INVENTION

In the prior art there may be found some 1-(dialkylaminoalkyl)-1,3-dihydro-2H-benzimidazol-2-ones including 1,3-dihydro-2H-benzimidazol-2-ones having antidepressant and anticonvulsant properties. Among other points of difference the compounds of this invention differ from such known compounds by the nature of the 4-substituted piperidine nucleus.

A number of the aforementioned prior art compounds may be found in the following references:
Int. Pharmacopsychiat. 1968 (1), p. 214;
C.A., 64, 2093b (1966); and
C.A., 72, 111466 (1970).

DESCRIPTION OF THE PREFERRED EMBODIMENTS:

The novel 1-benzazolylalkyl-4-substituted-piperidines of this invention may structurally be represented by the formula:

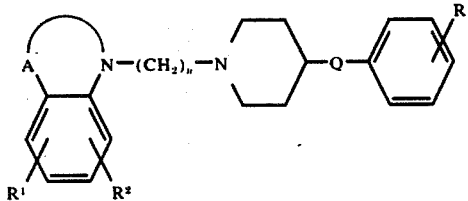
(I)

and the pharmaceutically acceptable acid addition salts thereof, wherein:

R is a member selected from the group consisting of hydrogen and halo;

$R^1$ and $R^2$ are each independently selected from the group consisting of hydrogen, halo, lower alkyl and trifluoromethyl;

n is an integer of from 2 to 4 inclusive;

Q is a member selected from the group consisting of

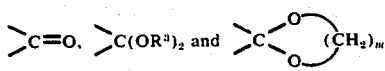

wherein $R^3$ is lower alkyl and m is an integer of from 2 to 3 inclusive; and

A is a bivalent radical selected from the group consisting of

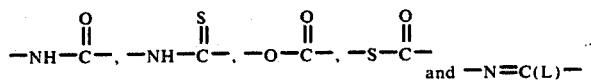

wherein L is selected from the group consisting of hydrogen, lower alkylthio, cycloalkyl and phenylmethyl, said bivalent radical being attached to the benzene nucleus by its heteroatom.

As used herein "lower alkyl" may be straight or branch chained and have from 1 to about 5 carbon atoms, such as, for example, methyl, ethyl, propyl, (1-methylethyl), butyl, pentyl and the like; and the term halo is generic to halogens of atomic weight less than 127; i.e., fluoro, chloro, bromo and iodo.

Compounds of formula (I) wherein R, $R^1$, $R^2$, Q and n are as previously defined and A is as previously defined but other than $$-NH-\overset{S}{\underset{\|}{C}}-,$$

said A being represented by $A^1$ and said compounds by the formula (I-a), can be prepared by reacting an appropriate intermediate of formula (II) wherein $R^1$, $R^2$, $A^1$ and n are as previously defined and wherein W is an appropriate reactive ester function derived from the corresponding alcohol, such as, for example, halo, methanesulfonyl, 4-methylbenzenesulfonyl and the like, with an appropriate piperidine derivative of formula (III) wherein Q and R are previously defined, according to common N-alkylating procedures known in the art.

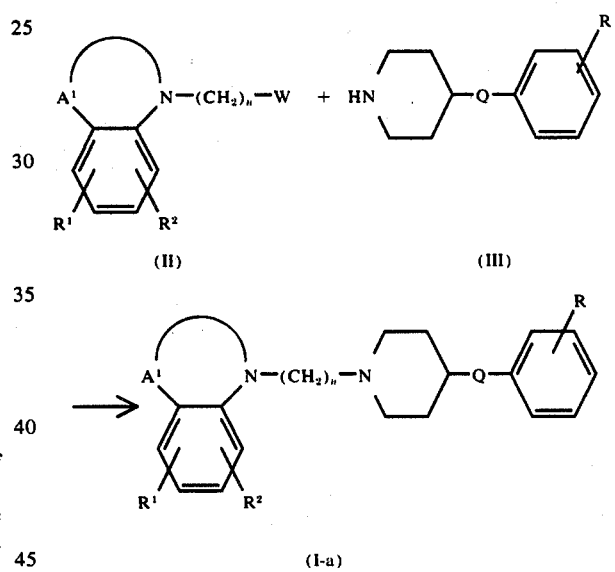

The foregoing condensation reaction is, carried out, preferably, in an appropriate organic solvent, such as, for example, a lower alkanol, e.g. methanol, ethanol, propanol, butanol and the like alcohols; and aromatic hydrocarbon, e.g. benzene, methylbenzene, dimethylbenzene, and the like; a ketone, e.g. 4-methyl-2-pentanone; an ether, e.g. 1,4-dioxane; 1,1'-oxybisethane and the like; N,N-dimethylformamide; nitrobenzene; and the like. The addition of an appropriate base, such as, for example, an alkali metal or earth alkali metal carbonate or hydrogen carbonate, may be utilized to pick up the acid that is liberated during the course of the reaction. A small amount of an appropriate metal iodide, e.g. sodium or potassium iodide, may be added as a reaction promotor, especially when the reactive ester of formula (II) is a chloride.

Somewhat elevated temperatures are appropriate to enhance the rate of the reaction and preferably the reaction is carried out at the reflux temperature of the reaction mixture. In this and following procedures, the reaction products are separated from the medium and, if necessary, further purified by the application of methodologies known in the art.

The compounds of formula (I) wherein R, R¹, R², n are as previously defined, Q is

and A is —NH—CO—, (I-b), may also be prepared starting from the corresponding intermediate of formula (IV) wherein P is an appropriate protecting group by the removal of the latter following conventional procedures. Examples of such protecting groups are, lower alkyloxycarbonyl and, a substituted ethenyl group of the formula:

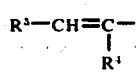

wherein $R^4$ and $R^5$ may represent different groups but wherein $R^4$ is preferably lower alkyl and $R^5$ is preferably hydrogen, lower alkyl or phenyl.

When the protecting group is a lower alkyloxycarbonyl group, it may easily be removed by alkaline hydrolysis, and when the protecting group is a substituted ethenyl group it is conveniently eliminated by subjecting the appropriate intermediate of formula (IV) to acid hydrolysis.

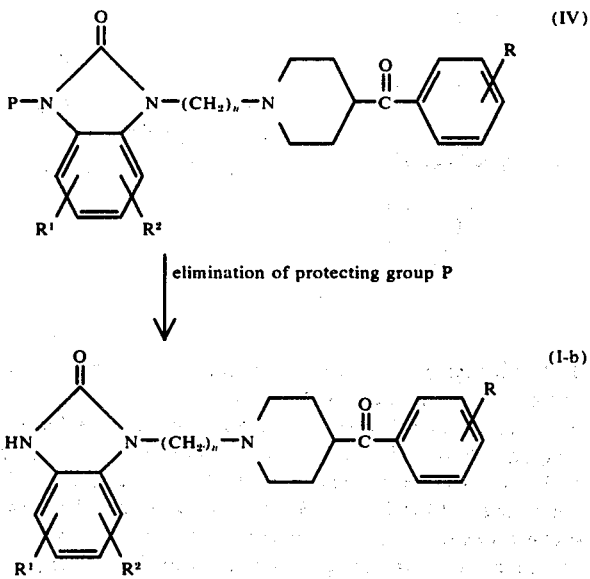

In carrying out the acid hydrolysis to remove the substituted ethenyl group from (IV) a wide variety of protonic acids may be employed including mineral acids, such as, for example, hydrochloric, hydrobromic, sulfuric, nitric and phosphoric acid, and organic acids, such as, for example, acetic acid, propanoic acid and the like. Further the reaction may be carried out in reaction-inert organic solvents as commonly employed in such a type of hydrolytic reactions, e.g. methanol, ethanol, 2-propanone and the like.

Compounds within the scope of formula (I) which may be represented by the formula:

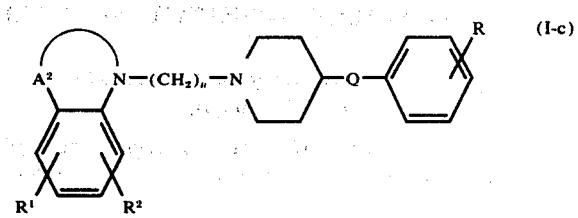

wherein R, R¹, R², n and Q are as previously defined and A² is selected from the group consisting of —NH—CO—, —NH—CS—; and —N=C(L¹)—wherein said L¹ is selected from the group consisting of hydrogen, cycloalkyl and phenylmethyl may still be prepared by subjecting an appropriate benzenediamine of formula (V) to ring closure with an appropriate cyclizing agent, the nature of which depends on the nature of A² in the desired product.

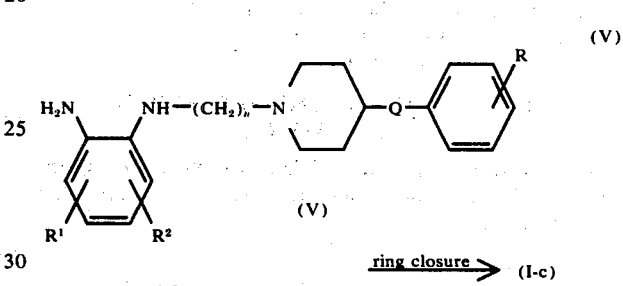

The foregoing cyclization reaction may be performed following art-known procedures of preparing 1H-benzimidazoles, 1,3-dihydro-2-H-benzimidazol-2-ones, and 1,3-dihydro-2H-benzimidazol-2-thiones starting from 1,2-benzenediamines. Suitable cyclizing agents which may advantageously be employed to prepare compounds (I-c) wherein A² stands for —NH—CO—, include, for example, urea, carbonyl dichloride and alkali metal isocyanates, and the cyclization reaction may be carried out following methodologies generally known in the art.

For example, when urea is used as the cyclizing agent the desired compounds are easily obtained by stirring and heating the reactants together in the absence of any solvent.

When A² in the desired compounds (I-c) stands for —NH—CS—, there may be used cyclizing agents such as, for example, carbon disulfide, thiourea, carbonothioic dichloride, ammonium thiocyanate and the like.

When A² stands for —N=C(L¹)— and when said L¹ is hydrogen there may be used formic acid or an appropriate tri(alkyloxy)methane as a cyclizing agent. When said L¹ in said —N=C(L¹)— is cycloalkyl or phenylmethyl, one may use as a cyclizing agent a carboxylic acid of the formula:

$$R^3—COOH \quad (VI)$$

wherein $R^5$ is respectively cycloalkyl or phenylmethyl, or a functional derivative thereof such as, for example, an acyl halide, an ester, an amide or a nitrile derived from such acid, or an iminoester of the formula:

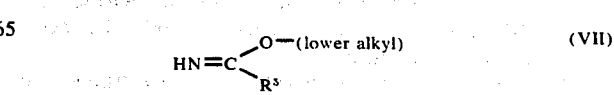

wherein R⁵ is as defined hereabove; or an aldehyde of the formula:

  (VIII)

or an addition product thereof with an alkali metal hydrogen sulfite. When the cyclizing agent is an aldehyde there may be added to the reaction mixture an appropriate oxidizing agent such as, for example, nitrobenzene, mercuric oxide, Cu(II) and Pb(II) salts or other suitable oxidants as known in the art, or the aldehyde itself, when added in excess may serve as an oxidant.

Compounds of formula (I) wherein A stands for

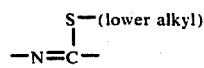

are also conveniently prepared starting from a corresponding compound (I) wherein A stands for —N—H—CS— by standard S-alkylating procedures, e.g., by the reaction of the thione with an appropriate halo-lower alkane in an appropriate organic solvent such as, for example, a lower alkanol, e.g., ethanol, propanol, 2-propanol, butanol and the like.

A number of the intermediates of formula (II) are known compounds and they may all be prepared following methodologies which are known per se. Depending on the nature of A¹ in said intermediates (II) the following procedures may be utilized for preparing them.

Intermediates of the formula (II-a)

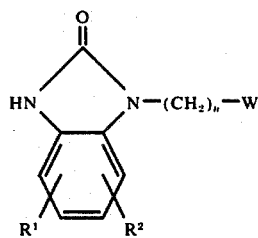  (II-a)

may be prepared as follows.

An appropriately substituted 2-chloronitrobenzene of formula (IX) is reacted with an appropriate aminoalkanol of formula (X) by refluxing the reactants together in an appropriate reaction-inert organic solvent such as, for example, a lower alkanol, preferably butanol, whereupon there is obtained a [(2-nitrophenyl)amino]alkanol of formula (XI), which in turn is subjected to a nitro-to-amine reduction, e.g., by catalytic hydrogenation using an appropriate catalyst such as, for example, Raney-nickel or palladium-on-charcoal. The thus obtained [(2-aminophenyl)amino]alkanol of formula (XII) is subsequently transformed into a 1,3-dihydro-1-(hydroxyalkyl)-2H-benzimidazol-2-one (XIII) by the reaction of (XII) with an alkali metal cyanate in aqueous medium or by stirring and heating (XII) with urea. The desired reactive esters of formula (II-a) are then easily obtained by converting the hydroxyl group of (XIII) into a reactive ester group by the application of generally known methodologies. Halides are conveniently prepared by the reaction of (XIII) with an appropriate halogenating agent such as, for example, sulfinyl chloride, sulfuryl chloride, phosphor pentachloride, phosphor pentabromide, phosphoryl chloride and the like. When the reactive ester is an iodide it is preferably prepared from the corresponding chloride or bromide by the replacement of that halogen with iodine. Other reactive esters such as methanesulfonates and 4-methylbenzenesulfonates are obtained by the reaction of the alcohol with an appropriate sulfonyl halide such as, for example, methanesulfonyl chloride and 4-methylbenzenesulfonyl chloride respectively.

The foregoing reactions are more clearly illustrated in the following schematic representation:

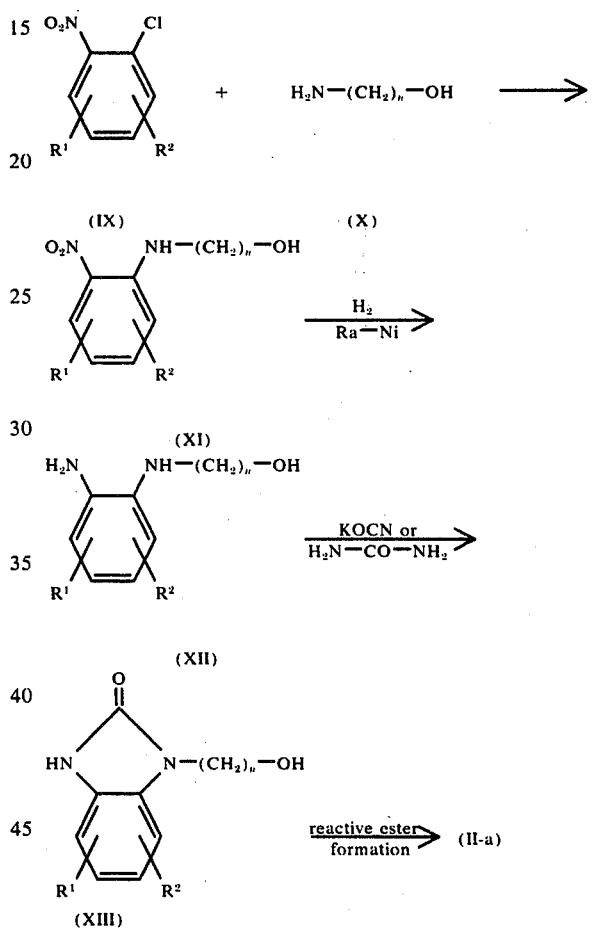

The intermediates (II-a) may alternatively be prepared by:

i. reacting an appropriately substituted 1,3-dihydro-2H-benzimidazol-2-one of formula (XIV) wherein R¹, R² and the protecting group P are as previously defined, with a haloalkanol of formula (XV) following common N-alkylating procedures to obtain an intermediate of formula (XVI);

ii. converting the hydroxyl function of (XVI) into a reactive ester group in the usual manner as previously described; and iii. eliminating the protecting group P of the thus obtained intermediate of formula (XVII) following the same procedures as described hereinbefore for the preparation of the compounds (I-b) starting from (IV).

The introduction of the hydroxyalkyl chain in (XIV) to obtain (XVI) may also be performed by the reaction of (XIV) with an appropriate 2-(haloalkyloxy)tetrahydro-2H-pyran, yielding as an intermediate the corresponding tetrahydro-2H-pyran-2-yl ether derivative of (XVI), the ether function of which is hydrolytically split open, e.g., by the treatment with an aqueous hydrochloric acid solution.

When the reactive ester (II-a) is a chloride, (II-a-1), if may alternatively be obtained by the reaction of (XIV) with a bromochloroalkane of formula (XVIII), yielding a 1-(chloroalkyl)-1,3-dihydro-3-P-2H-benzimidazol-2-one of formula (XVII-a), the protecting group of which is subsequently removed in the usual manner to yield the desired chloride (II-a-1). When in the preparation of the intermediates of formula (XVI), the hydroxyalkyl chain to be introduced is hydroxyethyl, the corresponding (XVI) may equally well be prepared by the reaction of (XIV) with oxirane in the presence of an appropriate strong metal base such as, e.g., sodium methanolate.

The foregoing reactions are illustrated by the follwoing schematic representation:

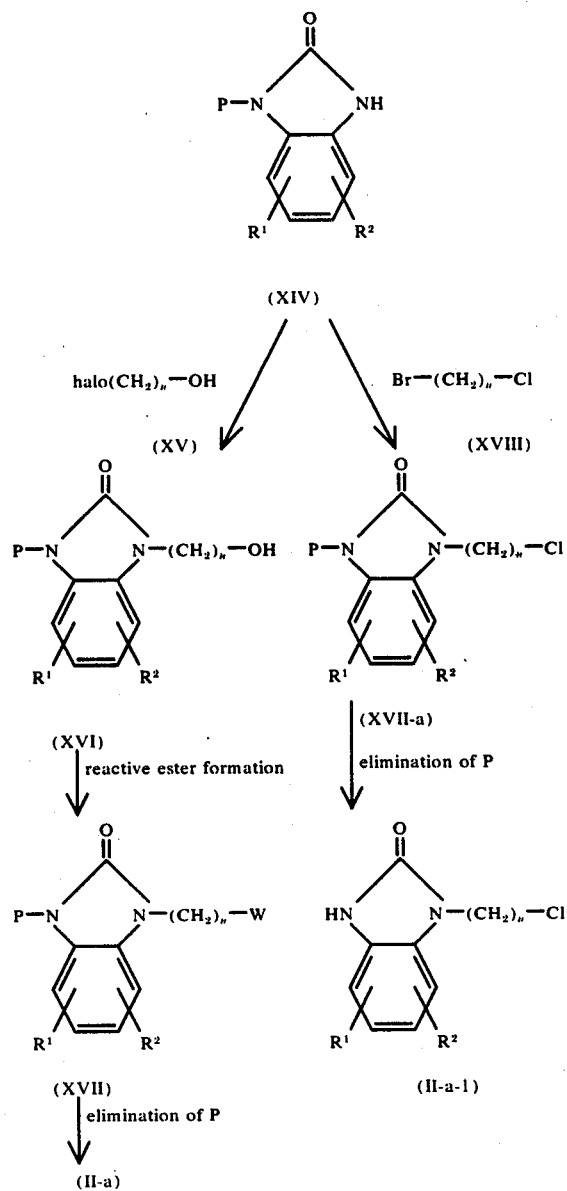

Intermediates of the formula (II-b)

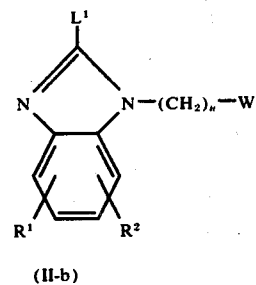

wherein $R^1$, $R^2$, $L^1$, n and W are as previously defined are conveniently obtained by the introduction of the reactive ester side chain into a starting material of the formula (XIX)

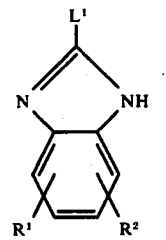

The introduction of the $(CH_2)_n$-W group may be performed following similar procedures to those described hereinbefore for the introduction of said group into starting materials of formula (XIV).

The intermediates of formula (II-b) may also be prepared by subjecting an appropriate hydroxyalkyl substituted benzenediamine of formula (XII) to ring closure with an appropriate cyclizing agent as described hereinabove, followed by the conversion of the hydroxyl group of the thus obtained intermediate of formula (XX) into a reactive ester group.

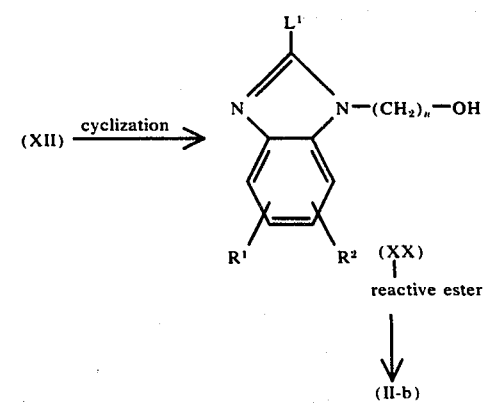

Intermediates of formula (II-c)

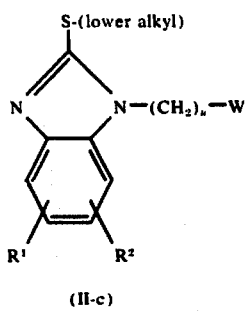

(II-c)

are conveniently obtained by first cyclizing an appropriate intermediate of formula (XII) with thiourea to obtain a 1,3-dihydro-2H-benzimidazol-2-thione of formula (XXI), S-alkylating the latter with an appropriate halo(lower alkane) in the usual manner and, finally, converting the hydroxyl group of the thus obtained (XXII) into a reactive ester group as previously defined.

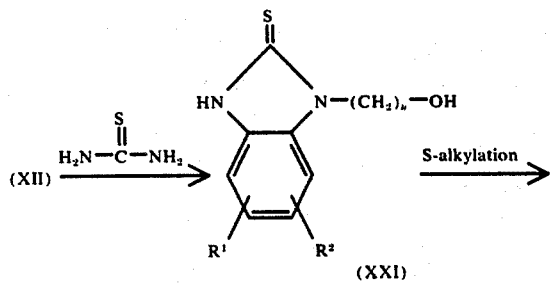

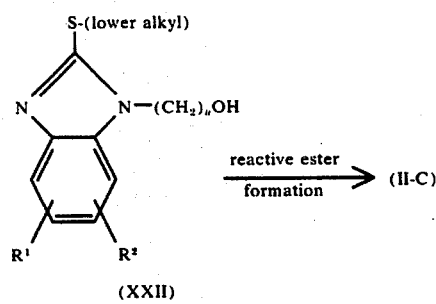

Intermediates of the formula (III) wherein Q stands for

(III-a), are generally known and may be prepared following art-known procedures. Those intermediates of formula (III) wherein Q stands for

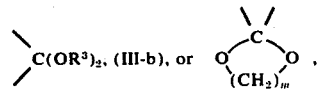

(III-c), can easily be derived from (III-a) by first N-acylating said (III-a) in the usual manner with an appropriate acyl halide, e.g., acetyl chloride, thereafter subjecting the thus obtained (XXIII) to a ketalization reaction with an appropriate lower alkanol (XXIV) or a alkanediol (XXV) to obtain a ketale of respectively formula (XXVI-a) or (XXVI-b), from which the desired intermediates (III-b) and (III-c) are easily obtained after hydrolytically splitting of the protecting acyl group in alkaline medium. The aforementioned ketalization reaction is conveniently carried out by stirring and refluxing the reactants together under azeotropic water removal in an appropriate organic solvent, preferably an aromatic hydrocarbon such as benzene, methylbenzene, dimethylbenzene and the like, in the presence of an appropriate strong acid, preferably 4-methylbenzenesulfonic acid.

The foregoing reactions are illustrated hereafter:

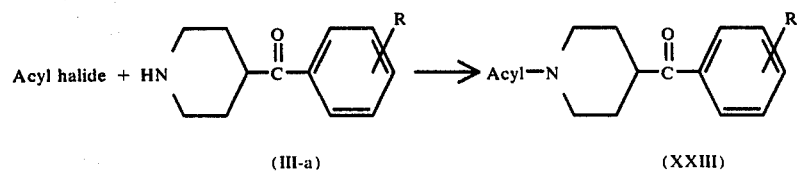

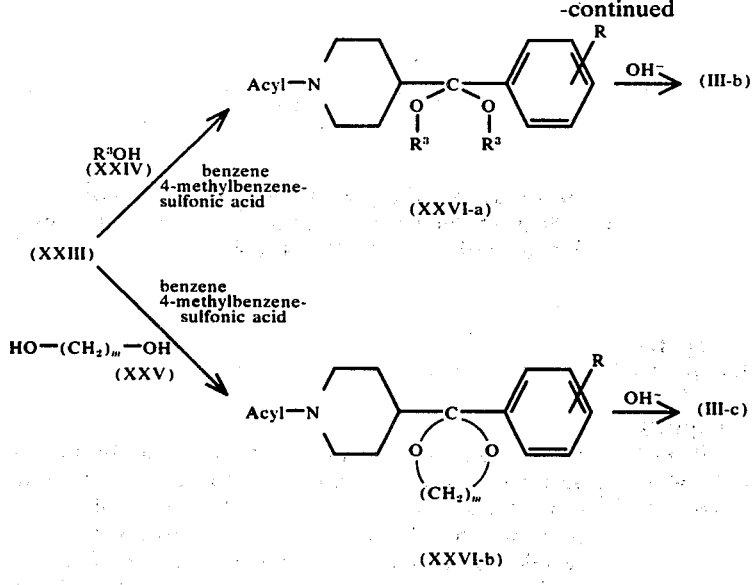

The intermediates of formula (IV) may be obtained by the condensation of a reactive ester of formula (XVII) with an intermediate of formula (III) wherein Q stands for

The intermediates of formula (V) are obtained by the condensation of an appropriate reactive ester of formula (XXVII) with a piperidine derivative of formula (III) followed by the reduction of the nitro group of the thus obtained intermediate (XXVIII) to an amino group according to standard nitro-to-amine reduction procedures, e.g., by the reaction of the compound with nascent hydrogen or by catalytic hydrogenation in the presence of an appropriate catalyst such as, for example, Raney-nickel.

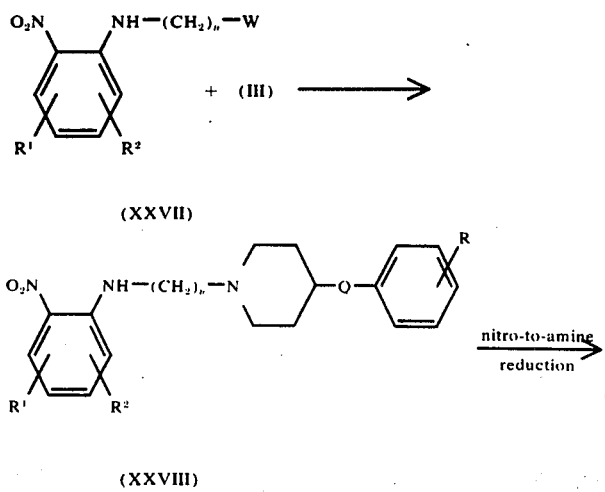

The reactive esters of formula (XXVII), used as starting materials herein, are easily prepared starting from an alcohol of formula (XI) by the conversion of the hydroxyl function thereof into a reactive ester group following standard procedures as previously described herein.

The compounds of the formulas (IV) and (V) are deemed to be novel and as useful intermediates in the preparation of the pharmaceutically useful compounds of formula (I) they constitute an additional feature of this invention.

The ultimate starting materials in each of the foregoing preparations are generally known and they may all be prepared following known methodologies as described in the literature.

The compounds of this invention may be converted to their therapeutically useful acid addition salts by treatment with an appropriate acid, such as, for example, an inorganic acid, such as, hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanedioic, (Z)-2-butenedioic, (E)-2-butenedioic, 2-hydroxybutanedioic,2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

The compounds of formula (I) and the therapeutically active acid addition salts thereof possess strong neuroleptic activity. Such neuroleptic activity is evidenced by the experimental data obtained in at least one of two different test procedures, viz., the combined apomorphine-tryptamine- and norepinephrine test in rats, and the apomorphine test in dogs. The tests were carried out following the procedures described hereafter and the experimental data which were obtained are summarized in the tables I, II and III. The compounds listed therein are not given for the purpose of limiting the invention thereto but only in order to exemplify the useful neuroleptic properties of all the compounds within the scope of formula (I).

A. The combined apomorphine-tryptamine- and norepinephrine test in rats.

The experimental animals used in this test were adult male Wistar rats (weight 240 ± 10g). After an overnight fast, the animals were treated subcutaneously (1 ml/100g) with an aqueous solution of the compound under investigation (time = zero) and put in isolated observation cages. Thirty minutes thereafter (time = 30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time = 90 minutes) the same animals were injected intravenously with 40 mg/kg of tryptamine (TRY) and the presence of the typical tryptamine-induced bilateral tonic seizures was noted. Two hours after pretreatment (time = 120 minutes) finally, the same animals were challenged with 1.25 mg/kg intravenously of norephinephrine (NOR) and possible mortality was looked for up to 60 minutes later. Table I and II give the lowest effective dose (LED) i.e., the dose level the effect of which was statistically significantly different from that observed in the corresponding untreated controls (Fisher exact probability test), for each of the three agonists studied (APO, TRY and NOR in the table).

B. The apomorphine test in dogs.

Neuroleptic drugs are known to inhibit emesis induced by apomorphine in dogs. The compounds listed in table III were administered either subcutaneously or orally to a minimum of a group of three beagle dogs. The animals were challenged 1, 4 or 16 hours after subcutaneous administration or 4 hours after oral administration with a standard dose of 0.31 mg/kg apomorphine hydrochloride (subcutaneously). This high dose of apomorphine induces emesis in all untreated control dogs.

Table III gives the $PD_{50}$-values (in mg/kg subcutaneously or orally), i.e., the dose of the compound protecting at the stated time half of the animals from emesis.

Table I:

Antiapomorphine (APO)-, antitryptamine (TRY)- and antinorepinephrine (NOR) activity of the listed compounds in rats.

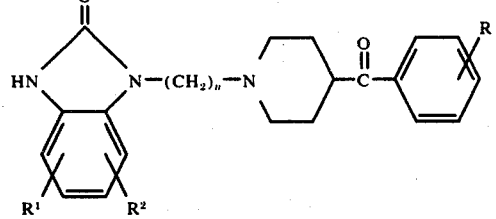

| Compound | n | R¹ | R² | R | LED (APO) in mg/kg s.c. | LED (TRY) in mg/kg s.c. | LED (NOR) in mg/kg s.c. |
|---|---|---|---|---|---|---|---|
| A | 2 | H | H | 4-F | 10 | 0.16 | 2.5 |
| B | 3 | H | H | 4-F | 0.04 | 0.08 | 2.5 |
| C | 3 | 5-Cl | H | 4-F | 0.08 | 0.16 | 5 |
| D | 3 | H | 6-Cl | 4-F | 0.31 | 0.08 | 5 |
| E | 3 | H | 7-Cl | 4-F | 1.25 | 1.25 | 2.5 |
| F | 3 | 5-Cl | 6-Cl | 4-F | 1.25 | 2.5 | >10 |
| G | 3 | 5-CH₃ | H | 4-F | 0.02 | 0.08 | 1.25 |
| H | 3 | 5-CF₃ | H | 4-F | 0.31 | 5 | >10 |
| I | 3 | 5-CH₃ | 6-CH₃ | 4-F | 0.63 | 2.5 | 5 |
| J | 4 | H | H | 4-F | 2.5 | 0.31 | 0.31 |
| K | 3 | H | H | 4-Cl | 2.5 | 5 | 5 |
| L | 3 | H | 6-CH₃ | 4-F | 0.31 | 0.63 | 10 |

Table II:

Antiapomorphine (APO)-, antitryptamine (TRY)- and antinorepinephrine (NOR)activity of the listed compounds in rats.

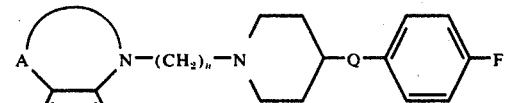

| Compound | R¹ | R² | n | Q | LED (APO) in mg/kg s.c. | LED (TRY) in mg/kg s.c. | LED (NOR) in mg/kg s.c. |
|---|---|---|---|---|---|---|---|
| M | (N-N fused) | | 3 | $-\overset{O}{\underset{\|}{C}}-$ | 0.16 | 1.25 | 0.63 |
| N | " | | 4 | $-\overset{O}{\underset{\|}{C}}-$ | 0.63 | 2.5 | 2.5 |

Table II:-continued
Antiapomorphine (APO)-, antitryptamine (TRY)- and anti-norepinephrine (NOR) activity of the listed compounds in rats.
| Compound | R¹ R² | n | Q | LED (APO) in mg/kg s.c. | LED (TRY) in mg/kg s.c. | LED (NOR) in mg/kg s.c. |
|---|---|---|---|---|---|---|
| O |  (benzothiazolone) | 3 | −C(=O)− | 0.31 | 1.25 | 2.5 |
| P | (2-thioxo-benzimidazole) | 3 | −C(=O)− | 0.02 | 0.04 | 1.25 |
| Q | (5-chloro-2-oxo-benzimidazole) | 3 | −C(−O−CH₂−CH₂−O−)− | 0.63 | 2.5 | — |
| R | 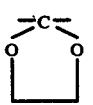 (2-cyclohexyl-benzimidazole) | 3 | −C(=O)− | 0.16 | 10 | 0.04 |

Table II:-continued

Antiapomorphine (APO)-, antitryptamine (TRY)- and anti-norepinephrine (NOR) activity of the listed compounds in rats.

| Compound | R¹ R² (structure) | n | Q | LED (APO) in mg/kg s.c. | LED (TRY) in mg/kg s.c. | LED (NOR) in mg/kg s.c. |
|---|---|---|---|---|---|---|
| S | 2-cyclohexyl-5-chloro-benzimidazolyl | 3 | $-\overset{O}{\underset{\|}{C}}-$ | 1.25 | — | 0.63 |
| T | 2-cyclohexyl-5-chloro-benzimidazolyl | 3 | $-\overset{O}{\underset{\|}{C}}-$ | 2.5 | — | 0.63 |
| U | 2-benzyl-benzimidazolyl | 3 | $-\overset{O}{\underset{\|}{C}}-$ | 0.31 | 1.25 | 2.5 |

Table III:

Antiapomorphine activity of the listed compounds in dogs.
Antiapomorphine effect in dogs: $PD_{50}$-values in mg/kg subcutaneously or orally at the stated time.

| Compound | After 1 hour (subcut.) | After 4 hours (subcut.) | After 4 hours (orally) | After 16 hours (subcut.) |
|---|---|---|---|---|
| A | 1.5 | — | — | — |
| B | 0.06 | — | 0.40 | — |
| C | 0.008 | 0.015 | 0.015 | 0.06 |
| D | 0.10 | — | — | — |
| E | 0.25 | — | — | — |
| F | 0.03 | 0.018 | 0.06 | 0.12 |
| G | 0.004 | 0.008 | 0.015 | 0.12 |
| H | 0.20 | 0.12 | — | — |

Table III:-continued

Antiapomorphine activity of the listed compounds in dogs.
Antiapomorphine effect in dogs: $PD_{50}$-values in mg/kg subcutaneously or orally at the stated time.

| Compound | After 1 hour (subcut.) | After 4 hours (subcut.) | After 4 hours (orally) | After 16 hours (subcut.) |
|---|---|---|---|---|
| I | 0.015 | 0.015 | 0.07 | — |
| J | 0.5 | — | — | — |
| K | 0.10 | — | — | — |
| L | 0.30 | 0.05 | 0.12 | — |
| M | 0.63 | — | — | — |
| N | 0.45 | — | — | — |
| O | 0.50 | 0.63 | — | — |
| P | 0.015 | 0.025 | 0.10 | — |
| Q | 0.10 | 0.03 | 0.03 | 0.06 |
| R | 0.63 | — | — | — |
| S | — | — | 0.25 | — |
| T | 0.50 | — | 0.16 | — |
| U | 0.80 | 1.0 | — | — |

The following examples are intended to illustrate and not to limit the invention thereto. Unless otherwise stated all parts therein are by weight.

A. PREPARATION OF INTERMEDIATES

Example I

To stirred mixture of 12.6 parts of 1,3-dihydro-1-(2-hydroxyethyl)-2H-benzimidazol-2-one, 10.1 parts of N,N-diethylethanamine and 195 parts of dichloromethane is added dropwise a solution of 9.2 parts of methanesulfonyl chloride in 13 parts of dichloromethane: exothermic reaction. Upon completion, stirring is continued for 1 hour at reflux temperature. The reaction mixture is cooled and poured onto water. The precipitated product is filtered off, washed with 2,2'-oxybispropane and crystallized from 4-methyl-2-pentanone (activated charcoal), yielding, after drying, 7.5 parts of 2-(2,3-dihydro-2-oxo-1H-benzimidazol-1-yl)ethyl methanesulfonate; mp. 156.7° C.

Example II

A mixture of 9 parts of 2-[(2-amino-4-chlorophenyl)amino]-ethanol and 9 parts of urea is stirred and heated for 2 hours at 180°-190° C. After cooling the reaction mixture is treated with concentrated sodium hydroxide solution. The obtained solution is filtered from some unsoluble matter. It is then treated with activated charcoal and filtered again. The filtrate is acidified with concentrated hydrochloric acid. After keeping overnight at room temperature, the precipitated solid is filtered off, washed and dried, to yield 5 parts of 5-chloro-1-(2-hydroxyethyl)-1,3-dihydro-2H-benzimidazol-2-one; mp. 176°-178.2° C; pale-brown, amorphous powder.

A mixture of 11 parts of 5-chloro-1-(2-hydroxyethyl)-1,3-dihydro-2H-benzimidazol-2-one, 25.5 parts of sulfinyl chloride and 150 parts of trichloromethane is stirred and refluxed for 20 hours.

The reaction mixture is filtered over hyflo and the filtrate is evaporated. The residue is boiled in 2-propanol. The undissolved part is filtered off and the filtrate is evaporated. The residue is crystallized from a mixture of 2-propanol and 2,2'-oxybispropane, yielding, after drying, 4.5 parts (38%) of 5-chloro-2-(2-chloroethyl)-1,3-dihydro-2H-benzimidazol-2-one; mp. 173.4° C.

Example III

A mixture of 20 parts of 2-[(2-amino-5-chlorophenyl)-amino]ethanol and 18 parts of urea is stirred and heated for 4 hours in an oil-bath at about 190° C. The reaction mixture is cooled and dissolved in alkaline water. The solution is acidified with a concentrated hydrochloric acid solution. The precipitated product is filtered off, washed with water and dried, yielding 13 parts (57.1%) of 6-chloro-1,3-dihydro-1-(2-hydroxyethyl)-2H-benzimidazol-2-one; mp. 160° C.

To a stirred mixture of 13 parts of 6-chloro-1,3-dihydro-1-(2-hydroxyethyl)-2H-benzimidazol-2-one in 225 parts of trichloromethane are added dropwise 32 parts of sulfinyl chloride. Upon completion, stirring is continued for 7 hours at reflux temperature. The reaction mixture is evaporated and the residue is triturated in water. The solid product is filtered off and crystallized from a mixture of 2-propanol and 2,2'-oxybispropane. It is filtered off again and dried, yielding 5 parts (35.5%) of 6-chloro-1-(2-chloroethyl)-1,3-dihydro-2H-benzimidazol-2-one; mp. 164° C.

Example IV

To a stirred mixture of 37.6 parts of 1,3-dihydro-6-methyl-1-(1-methylethenyl)-2H-benzimidazol-2-one, 2 parts of sodium methoxide solution 30% and 320 parts of absolute ethanol is added a solution of 22 parts of oxirane in 40 parts of absolute ethanol. Stirring is continued first overnight at room temperature and further for 3 hours at reflux. The ethanol is evaporated, yielding 46 parts (100%) of 1,3-dihydro-1-(2-hydroxyethyl)-5-methyl-3-(1-methylethenyl)-2H-benzimidazol-2-one as an oily residue.

To a stirred solution of 46 parts of 1,3-dihydro-1-(2-hydroxyethyl)-5-methyl-3-(1-methylethenyl)-2H-benzimidazol-2-one in 168 parts of ethanol are added 48 parts of hydrochloric acid solution and the whole is stirred for 2 hours at room temperature. The reaction mixture is evaporated and the residue is stirred in 250 parts of water. The precipitated product is filtered off, washed with 2,2'-oxybispropane and dried, yielding 22.3 parts (58%) of 1,3-dihydro-1-(2-hydroxyethyl)-5-methyl-2H-benzimidazol-2-one; mp. 158.7° C.

To a stirred mixture of 26 parts of 1,3-dihydro-1-(2-hydroxyethyl)-5-methyl-2H-benzimidazol-2-one and 390 parts of trichloromethane are added dropwise 48 parts of sulfinyl chloride at room temperature. Upon completion, stirring is continued for 5 hours at reflux. The reaction mixture is evaporated. The oily residue is heated with 2,2'-oxybispropane and a small amount of 2-propanol and the whole is stirred with activated charcoal. The latter is filtered off and the filtrate is stirred at room temperature till all the product is precipitated. It is filtered off and dried, yielding 12 parts (42%) of 1-(2-chloroethyl)-1,3-dihydro-5-methyl-2H-benzimidazol-2-one; mp. 120° C.

Example V

To a stirred solution of 8.5 parts of 1,3-dihydro-1-(1-methylethenyl)-2H-benzimidazol-2-one in 45 Parts of N,N-dimethylformamide are added portionwise 1.7 parts of sodium hydride dispersion 78%. After stirring for 1 hour at room temperature, the whole is cooled to 0°–5° C and 8.65 parts of 1-bromo-3-chloropropane are added dropwise (slowly). Upon completion, stirring is continued for 3 hours at room temperature. The reaction mixture is poured onto crushed ice and the product is extracted with methylbenzene. The extract is washed with water, dried, filtered and evaporated. The residue is crystallized from 2-propanol, yielding 5.5 parts (44%) of 1-(3-chloropropyl)-1,3-dihydro-3-(1-methylethenyl)-2H-benzimidazol-2-one; mp. 115° C.

Example VI

To a stirred and hot (±50° C) mixture of 34 parts of 1,3-dihydro-5-methyl-1-(1-methylethenyl)-2H-benzimidazol-2-one, 5 parts of N,N,N-triethylbenzenemethanaminium chloride and 300 parts of sodium hydroxide solution 50% are added 57 parts of 1-bromo-3-chloropropane (exothermic reaction: temperature rises to 70° C). The whole is stirred for 1 hour at 65°–70° C. The reaction mixture is cooled and poured onto crushed ice. The product is extracted with methylbenzene. The extract is washed three times with water, dried, filtered and evaporated. The oily residue is distilled yielding 40 parts (84%) of 3-(3-chloropropyl)-1,3-dihydro-5-methyl-1-(1-methylethenyl)-2H-benzimidazol-2-one; bp. 140° C at 0.02 mm. pressure.

Example VII

A mixture of 38.5 parts of 1,3-dihydro-1-(1-methyl-2-phenylethenyl)-2H-benzimidazol-2-one, 5 parts of N,N,N-triethylbenzenemethanaminium chloride and 225 parts of sodium hydroxide solution 60% is stirred and heated at 55° C. Then there are added dropwise 30.9 parts of 1-bromo-4-chlorobutane. Upon completion, stirring at 55° C is continued for 4 hours. The reaction mixture is cooled, water is added and the oily product is extracted with methylbenzene. The extract is dried, filtered and evaporated, yielding 53 parts of 1-(4-chlorobutyl)-1,3-dihydro-3-(1-methyl-2-phenylethenyl)-2H-benzimidazol-2-one as a residue.

A mixture of 52.5 parts of 1-(4-chlorobutyl)-1,3-dihydro-3-(1-methyl-2-phenylethenyl)-2H-benzimidazol-2-one, 220 parts of hydrochloric acid solution 6N and 240 parts of ethanol is stirred and refluxed for 6 hours. The reaction mixture is evaporated and the residue is dissolved in trichloromethane. The solution is dried, filtered and evaporated. The residue is crystallized from 2,2'oxybispropane, yielding, after drying, 25 parts (72.5%) of 1-(4-chlorobutyl)-1,3-dihydro-2H-benzimidazol-2-one; mp. 90° C.

Example VIII

A mixture of 100 parts of 1,2-dichloro-3-nitrobenzene, 95 parts of 3-amino-1-propanol and 200 parts of butanol is stirred and refluxed overnight. The reaction mixture is cooled and evaporated. The residue is taken up in water and the product is extracted with methylbenzene. The extract is washed with water, dried, filtered and evaporated, yielding 115 parts of 3-[(2-chloro-6-nitrophenyl)amino]-1-propanol as a residue.

Example IX

Following the procedure of Example VIII and using equivalent amounts of the appropriate starting materials there are prepared:
3-[(4,5-dichloro-2-nitrophenyl)amino]-1-propanol; mp. 97° C;
3-[(4-methyl-2-nitrophenyl)amino]-1-propanol as a residue; and
3-{[2-nitro-4-(trifluoromethyl)phenyl]amino}-1-propanol.

EXAMPLE X

A mixture of 70 parts of 3-[(4-methyl-2-nitrophenyl)amino]-1-propanol and 400 parts of methanol is hydrogenated at normal pressure and at room temperature with 10 parts of palladium-on-charcoal catalyst 10%. After the calculated amount of hydrogen is taken up, the catalyst is filtered off and the filtrate is evaporated, yielding 54 parts (91%) of 3-[(2-amino-4-methylphenyl)amino]-1-propanol as a residue.

Example XI

A mixture of 39.7 parts of 3-[(4,5-dichloro-2-nitrophenyl)amino]-1-propanol and 400 parts of methanol is hydrogenated at normal pressure and at room temperature with 5 parts of Raney-nickel catalyst. After the calculated amount of hydrogen is taken up, the catalyst is filtered off. The filtrate is acidified with 24 parts of a hydrochloric acid solution while stirring. The solvent is evaporated and the solid residue is stirred in 2-propanol. The product is filtered off and dried in vacuo, yielding 31.5 parts of 3-[(2-amino-4,5-dichlorophenyl)amino]-1-propanol hydrochloride; mp. ± 185° C.

Example XII

Following the procedure of Example XI the following 3-[(2-aminophenyl)amino]-1-propanols are prepared by hydrogenating the corresponding 3-[(2-nitrophenyl)amino]propanols:
3-[(2-amino-4-chlorophenyl)amino]-1-propanol as an oily residue;
3-[(2-amino-6-chlorophenyl)amino]-1-propanol as a residue; and
3-{[2-amino-4-(trifluoromethyl)phenyl]amino}-1-propanol.

Example XIII

To a stirred mixture of 31.2 parts of 3-[(2-amino-4,5-dichlorophenyl)amino]-1-propanol hydrochloride in 200 parts of water is added dropwise, during a 15 minutes-period, a solution of 10.6 parts of potassium cyanate in 50 parts of water at a temperature between 15° and 20° C. Upon completion, stirring is continued first for 20 minutes at room temperature and further for 20 hours at reflux. The reaction mixture is allowed to cool over week-end to room temperature. The precipitated product is filtered off and boiled in trichloromethane. The undissolved part is filtered off and boiled in 4-methyl-2-pentanone. After cooling, the product is filtered off and dried, yielding 14.5 parts (48%) of 5,6-dichloro-1,3-dihydro-1-(3-hydroxypropyl)-2H-benzimidazol-2-one; mp. 174.7° C.

Example XIV

Following the procedure of Example XIII the following 1,3-dihydro-1-(3-hydroxypropyl)-
2H-benzimidazol-2-ones are prepared starting from the appropriate 3-[(2-aminophenyl)amino]-1-propanols:

5-chloro-1,3-dihydro-1-(3-hydroxypropyl)-2H-benzimidazol-2-one; mp. 148.8° C;

1,3-dihydro-1-(3-hydroxypropyl)-5-methyl-2H-benzimidazol-2-one; mp. 114.1° C.

4-chloro-1,3-dihydro-3-(3-hydroxypropyl)-2H-benzimidazol-2-one; and 1,3-dihydro-1-(3-hydroxypropyl)-5-(trifluoromethyl)-2H-benzimidazol-2-one.

Example XV

To a stirred and refluxing (water-separator) mixture of 30 parts of 3-[(2-amino-4-chlorophenyl)amino]-1-propanol and 0.1 parts of 4-methylbenzenesulfonic acid in 405 parts of methylbenzene is added dropwise a solution of 34 parts of cyclohexanecarboxaldehyde in 45 parts of methylbenzene. Upon completion, stirring is continued for 1 hour at reflux temperature with water-separator. The methylbenzene is removed by evaporation in vacuo and the residue is triturated in 2,2'-oxybispropane. The product is filtered off and dried, yielding 16.5 parts (38%) of 5-chloro-2-cyclohexyl-1H-benzimidazole-1-propanol; mp. 95° C.

Example XVI

A mixture of 40 parts of 3-[(2-amino-5-chlorophenyl)amino]-1-propanol, 87 parts of sodium α-hydroxycyclohexanemethanesulfonate and 200 parts of ethanol is stirred and refluxed for 10 minutes. The reaction mixture is diluted with water and the solvent is evaporated. The residue is extracted a few times with trichloromethane. The combined extracts are dried, filtered and evaporated. The oily residue is triturated in 2,2'-oxybispropane: a sticky tar precipitates. The 2,2'-oxybispropane is decanted and upon stirring at room temperature, the product is allowed to precipitate. It is filtered off and dried, yielding 34 parts (58%) of 6-chloro-2-cyclohexyl-1H-benzimidazole-1-propanol; mp. 120.1° C.

Example XVII

Following the procedure of Example XVI there is prepared 5-chloro-2-(phenylmethyl)-1H-benzimidazole-1-propanol as a residue, by the reaction of 3-[(2-amino-4-chlorophenyl)amino]-1-propanol with sodium α-hydroxybenzeneethanesulfonate.

Example XVIII

A mixture of 30 parts of 1H-benzimidazole, 49 parts of 2-(4-chlorobutoxy)tetrahydro-2H-pyran, 21 parts of potassium hydroxide and 200 parts of ethanol is stirred and refluxed overnight. The reaction mixture is cooled to room temperature, filtered and the filtrate is evaporated. The residue is stirred in water and acidified with a diluted hydrochloric acid solution. The whole is stirred and heated for 30 minutes in a water-bath. After cooling to room temperature, the product is extracted with methylbenzene. The aqueous phase is separated and alkalized with ammonium hydroxide. The product is extracted with dichloromethane. The extract is dried, filtered and evaporated, yielding 50 parts of 1H-benzimidazole-1-butanolas as an oily residue.

Example XIX

To a stirred mixture of 22.6 parts of 6-chloro-1,3-dihydro-1-(3-hydroxypropyl)-2H-benzimidazol-2-one and 300 parts of trichloromethane are added dropwise 32 parts of sulfinyl chloride. Upon completion, stirring is continued for 3 hours at reflux. After stirring with activated charcoal, the reaction mixture is filtered hot over hyflo. The filtrate is evaporated and the residue is dissolved in methylbenzene. The solution is washed a few times with water, dried, filtered and evaporated. The oily residue is triturated in 2,2'-oxybispropane. The solid product is filtered off and dried, yielding 19 parts (77.5%) of 6-chloro-1-(3-chloropropyl)-1,3-dihydro-2H-benzimidazol-2-one; mp. 122° C.

Example XX

Following the procedure of Example XIX and using an equivalent amount of an appropriately substituted 1,3-dihydro-1-(hydroxyalkyl)-2H-benzimidazol-2-one or 1H-benzimidazole-1-alkanol as a starting material there are prepared:

1-(3-chloropropyl)-1,3-dihydro-5-(trifluoromethyl)-2H-benzimidazol-2-one;

1-(4-chlorobutyl)-1H-benzimidazole as an oily residue;

5-chloro-1-(3-chloropropyl)-2-cyclohexyl-1H-benzimidazole hydrochloride; mp. 211.7° C;

6-chloro-1-(3-chloropropyl)-2-cyclohexyl-1H-benzimidazole hydrochloride; mp. 227.5° C;

1-(3-chloropropyl)-2-(phenylmethyl)-1H-benzimidazole; mp. 112° C; and 5-chloro-1-(3-chloropropyl)-2-(phenylmethyl)-1H-benzimidazole as a solid residue.

Example XXI

To a stirred solution of 18.5 parts of 1,3-dihydro-1-(3-hydroxypropyl)-5-methyl-2H-benzimidazol-2-one in 325 parts of dichloromethane are added 11.9 parts of N,N-diethylethanamine. Then there are added dropwise (slowly) 11.5 parts of methanesulfonyl chloride. Upon completion, stirring is continued for 1 hour at reflux temperature. After cooling, the reaction mixture is washed with water, dried, filtered and evaporated. The solid residue is crystallized from 4-methyl-2-pentanone, yielding 15 parts (58%) of 3-(2,3-dihydro-5-methyl-2-oxo-1H-benzimidazol-1-yl)propyl methanesulfonate; mp 125° C.

EXAMPLE XXII

Following the procedure of Example XXI the following methanesulfonates are derived from the corresponding alcohols:

3-(5-chloro-2,3-dihydro-2-oxo-1H-benzimidazol-1-yl)propyl methanesulfonate; mp. ± 140° C;

3-(7-chloro-2,3-dihydro-2-oxo-1H-benzimidazol-1-yl)propyl methanesulfonate; and 3-(5,6-dichloro-2,3-dihydro-2-oxo-1H-benzimidazol-1-yl)propyl methanesulfonate as an oily residue.

EXAMPLE XXIII

A mixture of 8.2 parts of 2-(methylthio)-1H-benzimidazole, 16 parts of 1-bromo-3-chloropropane, 5.3 parts of sodium carbonate and 200 parts of 4-methyl-2-pentanone is stirred and refluxed for 44 hours. After cooling, water is added and the layers are separated. The organic phase is dried, filtered and evaporated. The residue is stirred in 2,2'-oxybispropane. The unreacted starting material is filtered off and the filtrate is evaporated, yielding 6 parts (50%) of 1-(3-chloropropyl)-2-(methylthio)-1H-benzimidazole as an oily residue.

EXAMPLE XXIV

To a stirred and hot (55° C) mixture of 22.2 parts of 1,3-dihydro-5,6-dimethyl-3-(1-methyl-2-phenylethenyl)-2H-benzimidazol-2-one, 3 parts of N,N,N-triethylbenzenemethanaminium chloride and 112.5 parts of sodium hydroxide solution 60% are added dropwise 15.8 parts of 1-bromo-3-chloropropane (slightly exothermic reaction). Upon completion, stirring is continued for 5 hours at 55° C. After cooling, water is added and the oily product is extracted with methylbenzene. The extract is dried, filtered and evaporated. The residue is crystallized from 2,2'-oxybispropane, yielding, after drying, 25 parts (88.5%) of 1-(3-chloropropyl)-1,3-dihydro-5,6-dimethyl-3-(1-methyl-2-phenylethenyl)-2H-benzimidazol-2-one; mp. 98° C.

EXAMPLE XXV

Following the procedure of Example XXIV and using an equivalent amount of 2-cyclohexyl-1H-benzimidazole in place of the 1,3-dihydro-5,6-dimethyl-3-(1-methyl-2-phenylethenyl)-2H-benzimidazol-2-one used therein, there is prepared:
1-(3-chloropropyl)-2-cyclohexyl-1H-benzimidazole as an oil residue.

EXAMPLE XXVI

A mixture of 25 parts of 1-(3-chloropropyl)-1,3-dihydro-5,6-dimethyl-3-(1-methyl-2-phenylethenyl)-2H-benzimidazol-2-one, 165 parts of a hydrochloric acid solution 6N and 160 parts of ethanol is stirred and refluxed for 6 hours. The reaction mixture is evaporated and the residue is dissolved in trichloromethane. This solution is dried, filtered and evaporated. The residue is crystallized from a mixture of 2,2'-oxybispropane and 2-propanol, yielding, after drying, 16 parts (94.7%) of 1-(3-chloropropyl)-1,3-dihydro-5,6-dimethyl-2H-benzimidazol-2-one; mp. 140° C.

EXAMPLE XXVII

To a stirred mixture of 39.2 parts of 3-(2-nitrophenyl)amino-1-propanol and 225 parts of trichloromethane are added dropwise 35.7 parts of sulfinyl chloride (exothermic reaction: temperature rises to 45° C). Upon completion, stirring is continued for 6 hours at reflux temperature. The reaction mixture is evaporated, yielding 43 parts (100%) of N-(3-chloropropyl)-2-nitrobenzenamine as a residue.

A mixture of 26.6 parts of N-(3-chloropropyl)-2-nitrobenzenamine, 24.35 parts of (4-fluorophenyl)(4-piperidinyl)methanone hydrochloride, 21.2 parts of sodium carbonate, 0.2 parts of potassium iodide and 200 parts of 4-methyl-2-pentanone is stirred and refluxed for 24 hours with water-separator. The reaction mixture is cooled, water is added and the layers are separated. The organic phase is dried, filtered and evaporated, yielding 27 parts (70%) of (4-fluorophenyl) [1-{3-[(2-nitrophenyl)amino]propyl}-4-piperidinyl]methanone as a residue.

A mixture of 27 parts of (4-fluorophenyl) [1-{3-[(2-nitrophenyl)amino]propyl}-4-piperidinyl]methanone in 400 parts of methanol is hydrogenated at normal pressure and at room temperature with 5 parts of Raney-nickel catalyst. After the calculated amount of hydrogen is taken up, the catalyst is filtered off over hyflo and the filtrate is evaporated, yielding 25 parts (100%) of [1-{3-[(2-aminophenyl)amino]-propyl}-4-piperidinyl] (4-fluorophenyl)methanone as a residue.

EXAMPLE XXVIII

A mixture of 5.3 parts of 3-(3-chloropropyl)-1,3-dihydro-5-methyl-1-(1-methylethenyl)-2H-benzimidazol-2-one, 4.9 parts of (4-fluorophenyl)(4-piperidinyl)methanone hydrochloride, 8.5 parts of sodium carbonate, 0.2 parts of potassium iodide and 200 parts of 4-methyl-2-pentanone is stirred and refluxed overnight with water-separator. The reaction mixture is cooled, water is added and the layers are separated. The 4-methyl-2-pentanone phase is dried, filtered and evaporated. The residue is purified by column-chromatography over silica gel using a mixture of trichloromethane and methanol (95:5 by volume) as eluent. The pure fractions are collected and the eluent is evaporated, yielding 4.5 parts (52%) of 3-{3-[4-(4-fluorobenzoyl)-1-piperidinyl]propyl}-1,3-dihydro-5-methyl-1-(1-methylethenyl)-2H-benzimidazol-2-one as an oily residue.

EXAMPLE XXIX

A mixture of 74.7 parts of 1-acetyl-4-[-4-fluorophenyl)carbonyl]piperidine, 46.5 parts of 1,2-ethanediol, 3 parts of 4-methylbenzenesulfonic acid and 810 parts of benzene is stirred and refluxed for 108 hours with water-separator. The reaction mixture is cooled and washed successively with a mixture of 250 parts of water and 22.5 parts of ammonium hydroxide, and with 250 parts of water. The organic phase is separated, dried, filtered and evaporated. The residue is purified by column-chromatography over silica gel using a mixture of trichloromethane and 2-propanone (50:50 by volume) as eluent. The pure fractions are collected and the eluent is evaporated, yielding 50 parts (56.8%) of 1-acetyl-4-[2-(4-fluorophenyl)-1,3-dioxolan-2-yl]piperidine as a residue.

A mixture of 5 parts of 1-acetyl-4-[2-(4-fluorophenyl)-1,3-dioxolan-2-yl]piperidine and 100 parts of sodium hydroxide solution 10% is stirred and refluxed overnight. The reaction mixture is cooled and the product is extracted with trichloromethane. The extract is dried, filtered and evaporated. The solid residue is stirred in 2,2'-oxybispropane. The product is filtered off and dried in vacuo at 40° C, yielding 3.5 parts (82%) of 4-[2(4-fluorophenyl)-1,3-dioxolan-2-yl]-piperidine.

B. PREPARATION OF FINAL PRODUCTS

EXAMPLE XXX

A mixture of 5.6 parts of 2-(2,3-dihydro-2-oxo-1H-benzimidazol-1-yl)ethyl methanesulfonate, 4.9 parts of (4-fluorophenyl) (4-piperidinyl) methanone hydrochloride, 8 parts of sodium carbonate and 200 parts of 4-methyl-2-pentanone is stirred and refluxed for 7 hours with water-separator. After cooling, water is added and the layers are separated. The organic phase is dried, filtered and evaporated. The oily residue is purified by column-chromatography over silica gel using a mixture of trichloromethane and 10% of methanol as eluent. The pure fractions are collected and the eluent is evaporated. The residue is crystallized from 4-methyl-2-pentanone, yielding 4.3 parts of 1-{2-[4-(4-fluorobenzoyl)-1-piperidinyl]ethyl}-1,3-dihydro-2H-benzimidazol-2-one; mp. 163.6° C.

EXAMPLE XXXI

A mixture of 5 parts of 1-(3-chloropropyl)-1,3-dihydro-3-(1-methylethenyl)-2H-benzimidazol-2-one, 4.5 parts of (4-fluorophenyl) (4-piperidinyl) methanone, 10 parts of sodium carbonate, 0.2 parts of potassium iodide and 80 parts of 4-methyl-2-pentanone is stirred and refluxed overnight. After cooling, the reaction mixture is poured onto water and the layers are separated. The organic phase is dried, filtered and evaporated. The residue is taken up in 2-propanone and 2-propanol, previously saturated with gaseous hydrogen chloride, is added. After boiling for 30 minutes, the mixture is evaporated. A diluted hydrochloric acid solution is added to the residue and the whole is stirred and warmed at 40°–45° C for 1 hour. After the addition of 4-methyl-2-pentanone, the mixture is alkalized with ammonium hydroxide and the layers are separated. The organic phase is dried, filtered and and evaporated. The residue is crystallized from 4-methyl-2-pentanone. The product is filtered off and dried, yielding 1.5 parts (20%) of 1-{3-[4-(4-fluorobenzoyl)-1-piperidinyl]propyl}-1,3-dihydro-2H-benzimidazol-2-one; mp. 163.9° C.

Example XXXII

A mixture of 5.5 parts of 3-(5-chloro-2,3-dihydro-2-oxo-1H-benzimidazol-1-yl)propyl methanesulfonate, 3.6 parts of (4-fluorophenyl) (4-piperidinyl) methanone, 6 parts of sodium carbonate and 80 parts of 4-methyl-2-pentanone is stirred and refluxed overnight. After cooling, the reaction mixtue is filtered and the filtrate is evaporated. The residue is purified by column-chromatography over silica gel using a mixture of trichloromethane and 5% of methanol as eluent. The pure fractions are collected and the eluent is evaporated. The residue is crystallized from 4-methyl-2-pentanone. The product is filtered off and recrystallized from 4-methyl-2-pentanone, yielding 0.6 parts (10%) of 5-chloro-1-{3-[4-(4-fluorobenzoyl)-1-piperidinyl]-propyl}-1,3-dihydro-2H-benzimidazol-2-one; mp. 163.7° C.

Example XXXIII

A mixture of 5.6 parts of 6-chloro-1-(3-chloropropyl)-1,3-dihydro-2H-benzimidazol-2-one, 4.9 parts of (4-fluorophenyl) (4-piperidinyl) methanone hydrochloride, 8.5 parts of sodium carbonate, 0.2 parts of potassium iodide and 200 parts of 4-methyl-2-pentanone is stirred and refluxed overnight with water-separator. After cooling, water is added and the layers are separated. The 4-methyl-2-pentanone-phase is dried, filtered and evaporated. The residue is purified by column-chromatography over silica gel using a mixture of trichloromethane and 5% of methanol as eluent. The pure fractions are collected and the eluent is evaporated. The residue is crystallized from 2-propanol, yielding 1.9 parts (23%) of 6-chloro-1-{3-[4-(4-fluorobenzoyl)-1-piperidinyl]propyl}-1,3-dihydro-2H-benzimidazol-2-one; mp. 157° C.

Example XXXIV

A mixture of 4.4 parts of 3-(7-chloro-2,3-dihydro-2-oxo-1H-benzimidazol-1-yl)propyl methanesulfonate, 3.4 parts of (4-fluorophenyl) (4-piperidinyl) methanone hydrochloride, 5 parts of sodium carbonate and 45 parts of N,N-dimethylformamide is stirred for 6 hours at 50-60° C. The reaction mixture is cooled and poured onto water. The product is extracted with 4-methyl-2-pentanone. The extract is dried, filtered and evaporated. The residue is purified by column-chromatography over silica gel using a mixture of trichloromethane and 10% of methanol as eluent. The pure fractions are collected and the eluent is evaporated. The residue is crystallized from a mixture of 4-methyl-2-pentanone and 2,2'-oxybispropane, yielding 1 part (18%) of 4-chloro-3-{3-[4-(4-fluorobenzoyl)-1-piperidinyl]-propyl}-1,3-dihydro-2H-benzimidazol-2-one; mp. 138° C.

Example XXXV

A mixture of 4.4 parts of (4-fluorophenyl) (4-piperidinyl) methanone hydrochloride, 6 parts of sodium carbonate and 160 parts of 4-methyl-2-pentanone is stirred and refluxed for 30 minutes with water-separator. After cooling, 6.2 parts of 3-(5,6-dichloro-2,3-dihydro-2-oxo-1H-benzimidazol-1yl)propyl methanesulfonate are added and the whole is stirred and refluxed overnight. The reaction mixture is cooled, water is added and the layers are separated. The 4-methyl-2-pentanone-phase is dried, filtered and evaporated. The solid residue is purified by column-chromatography over silica gel using a mixture of trichloromethane and 10% of methanol as eluent. The pure fractions are collected and the eluent is evaporated. The solid residue is stirred in trichloromethane. The product is filtered off, stirred in methanol, filtered off again and dried, yielding 2 parts (25%) of 5,6-dichloro-1-{3-[4-(4-fluorobenzoyl)-1-piperidinyl]propyl}-1,3-dihydro-2H-benzimidazol-2-one; mp. 198° – 202° C.

Example XXXVI

A mixture of 5.68 parts of 3-(2,3-dihydro-5-methyl-2-oxo-1H-benzimidazol-1-yl)propyl methanesulfonate, 4.8 parts of (4-fluorophenyl) (4-piperidinyl) methanone hydrochloride, 3.7 parts of sodium carbonate and 45 parts of N,N-dimethylformamide is stirred for 1 hour at 50°–60° C. The reaction mixture is cooled to room temperature and poured onto water. The product is extracted with trichloromethane. The extract is dried, filtered and evaporated. The residue is purified by column-chromatography over silica gel using a mixture of trichloromethane and 10% of methanol as eluent. The pure fractions are collected and the eluent is evaporated. The residue is crystallized from 4-methyl-2-pentanone. The product is filtered off and recrystalized twice from 4-methyl-2-pentanone, yielding 0.5 parts (6.5%) of 1-{3-[4-(4-fluorobenzoyl)-1-piperidinyl]propyl}-1,3-dihydro-5-methyl-2H-benzimidazol-2-one; mp. 149° C.

Example XXXVII

A mixture of 4.2 parts of 1-(3-chloropropyl)-1,3-dihydro-5-(trifluoromethyl)-2H-benzimidazol-2-one, 3.6 parts of (4-fluorophenyl) (4-piperidinyl) methanone hydrochloride, 10 parts of sodium carbonate, 0.1 parts of potassium iodide and 80 parts of 4-methyl-2-pentanone is stirred and heated till reflux. Refluxing is continued overnight. After cooling to room temperature, the reaction mixture is poured onto water. The organic phase is separated, dried, filtered and evaporated. The residue is purified by column-chromatography over silica gel using a mixture of trichloromethane and 10% of methanol as eluent. The pure fractions are collected and the eluent is evaporated. The residue is crystallized from a mixture of 4-methyl-2-pentanone and 2,2-oxybispropane, yielding 1.4 parts (20%) of 1-{3-[4-(4-fluorobenzoyl)-1-piperidinyl]propyl}-1,3-dihydro-5-(trifluoromethyl)-2H-benzimidazol-2-one; mp. 160.2° C.

Example XXXVIII

A mixture of 4.76 parts of 1-(3-chloropropyl)-1,3-dihydro-5,6-dimethyl-2H-benzimidazol-2-one, 4.87 parts of (4-fluorophenyl) (4-piperidinyl) methanone hydrochloride, 6.36 parts of sodium carbonate, 0.2 parts of potassium iodide and 200 parts of 4-methyl-2-pentanone is stirred and refluxed for 20 hours with water-separator. After cooling, water is added. The undissolved product is filtered off, washed with 4-methyl-2-pentanone and crystallized from ethanol, yielding, after drying, 5 parts (61%) of 1-{3-[4-(4-fluorobenzoyl)-1-piperidinyl]propyl}-1,3-dihydro-5,6-dimethyl-2H-benzimidazol-2-one; mp. 195.3° C.

Example XXXIX

A mixture of 4 parts of 1-(4-chlorobutyl)-1,3-dihydro-2H-benzimidazol-2-one, 4 parts of (4-fluorophenyl) (4-piperidinyl) methanone hydrochloride, 10 parts of sodium carbonate, 0.2 parts of potassium iodide and 80 parts of 4-methyl-2-pentanone is stirred and refluxed overnight. After cooling, water is added and the layers are separated. The organic phase is dried, filtered and evaporated. The solid residue is purified by column-chromatography over silica gel using a mixture of trichloromethane and 10% of methanol as eluent. The pure fractions are collected and the eluent is evaporated. The residue is crystallized from 4-methyl-2-pentanone, yielding 2 parts (30%) of 1-{4-[4-(4-fluorobenzoyl)-1-piperidinyl]butyl}-1,3-dihydro-2H-benzimidazol-2-one; mp. 176.5° C.

Example XL

Following the procedure of Example XXXIII and using therein an equivalent amount of an appropriate 1-(2-chloroethyl)-1,3-dihydro-2H-benzimidazol-2-one in place of the 6-chloro-1-(3-chloropropyl)-1,3-dihydro-2H-benzimidazol-2-one, the following compounds are prepared:
5-chloro-1-{2-[4-(4-fluorobenzoyl)-1-piperidinyl]ethyl}-1,3-dihydro-2H-benzimidazol-2-one; and
6-chloro-1-{2-[4-(4-fluorobenzoyl)-1-piperidinyl]ethyl}-1,3-dihydro-2H-benzimidazol-2-one.

Example XLI

Following the procedure of Example XXXI and using an equivalent amount of 3-(3-chloropropyl)-1,3-dihydro-5-methyl-1-(1-methylethenyl)-2H-benzimidazol-2-one in place of the 1-(3-chloropropyl)-1,3-dihydro-3-(1-methylethenyl)-2H-benzimidazol-2-one used therein, there is obtained:
1-{3-[4-(4-fluorobenzoyl)-1-piperidinyl]propyl}-1,3-dihydro-6-methyl-2H-benzimidazol-2-one.

Example XLII

A mixture of 4.5 parts of 3-{3-[4-(4-fluorobenzoyl)-1-piperidinyl]propyl}-1,3-dihydro-5-methyl-1-(1-methylethenyl)-2H-benzimidazol-2one, 24 parts of a concentrated hydrochloric acid solution, 80 parts of ethanol and 50 parts of water is stirred for 2 hours at room temperature. The reaction mixture is evaporated and the residue is stirred in water. The whole is alkalized with ammonium hydroxide. The product is extracted with trichloromethane. The extract is dried, filtered and evaporated. The oily residue is purified by column-chromatography over silica gel using a mixture of trichloromethane and methanol (95:5 by volume) as eluent. The pure fractions are collected and the eluent is evaporated. The residue is crystallized from 4-methyl-2-pentanone, yielding 1 part (25%) of 1-{3-[4-(4-fluorobenzoyl)-1-piperidinyl]propyl}-1,3-dihydro-6-methyl-2H-benzimidazol-2-one; mp. 149.7° C

Example XLIII

A mixture of 25 parts of [1-{3-[2-aminophenyl)amino]propyl}-4-piperidinyl](4-fluorophenyl)methanone, 65 parts of carbon disulfide and 80 parts of ethanol is stirred and refluxed for 15 hours. The reaction mixture is evaporated. The residue is purified by column-chromatography over silica gel using a mixture of trichloromethane and methanol (95:5 by volume) as eluent. The pure fractions are collected and the eluent is evaporated. The residue is crystallized from 2-propanol. The product is filtered off and dried, yielding 5 parts (18%) of {1-[3-(2,3-dihydro-2-thioxo-1H-benzimidazol-1-yl)propyl]-4-piperidinyl}(4-fluorophenyl)methanone; mp. 149.2° C.

Example XLIV

Following the procedure of Example XXXIX and using equivalent amounts of the appropriate starting materials, the following compounds are prepared:
3-{3-[4-(4-flouorobenzoyl)-1-piperidinyl]propyl}-2(3H)-behzoxazolone; mp. 145.2° C;
{1-[2-(1H-benzimidazol-1-yl)ethyl]-4-piperidinyl}(4-fluorophenyl)-methanone; mp. 119.2° C;
{1-[3-(1H-benzimidazol-1-yl)propyl]-4-piperidinyl}(4-fluorophenyl)-methanone; mp. 129.4° C;
{1-[4-(1H-benzimidazol-1-yl)butyl]-4-piperidinyl}(4-fluorophenyl)-methanone; mp. 112.9° C;
{1-[3-(2-cyclohexyl-1H-benzimidazol--1-yl)propyl]-4-piperidinyl}(4-fluorophenyl)methanone; mp. 105.5° C;
{1-[3-(5-chloro-2-cyclohexyl-1H-benzimidazol-1-yl)propyl]-4-piperidinyl}(4-fluorophenyl)methanone; mp. 103.6° C; and
{1-[3-(6-chloro-2-cyclohexyl-1H-benzimidazol-1-yl)propyl]-4-piperidinyl}(4-fluorophenyl)methanone; mp. 116.8° C.

Example XLV

Following the procedure of Example XXXVIII and using equivalent amounts of the appropriate starting materials, the following compounds are prepared:
(4-fluorophenyl)[1-{3-[2-(methylthio)-1H-benzimidazol-1-yl]propyl}-4-piperidinyl]methanone; mp. 112.2° C;
(4-fluorophenyl)[1-{3-[2-(phenylmethyl)-1H-benzimidazol-1-yl]propyl}-4-piperidinyl]methanone; mp. 133.3° C; and
[1-{3-[5-chloro-2-(phenylmethyl)-1H-benzimidazol-1-yl]propyl}-4-piperidinyl](4-fluorophenyl)methanone; mp. 95.8° C.

Example XLVI

Following the procedure of Example XXXII there is prepared 1-{3-[4-(4-chlorobenzoyl)-1-piperidinyl]propyl}-1,3-dihydro-2H-benzimidazol-2-one; mp. 170.8° C, by the reaction of 1,3-dihydro-1-(3-hydroxypropyl)-

2H-benzimidazol-2-one methanesulfonate with (4-chlorophenyl) (4-piperidinyl) methanone.

Example XLVII

A mixture of 6 parts of 3-(3-bromopropyl)-2,3-dihydro2(3H)-benzothiazolone, 4.87 parts of (4-fluorophenyl) (4-piperidinyl) methanone hydrochloride, 5.3 parts of sodium carbonate and 200 parts of 4-methyl-2-pentanone is stirred and refluxed for 20 hours with water-separator. The reaction mixture is cooled, water is added and the layers are separated. The organic phase is dried, filtered and evaporated. The residue is crystallized from 2,2'-oxybispropane. The product is filtered off and dried, yielding 3 parts (37.6%) of 3-{3-[4-(4-fluorobenzoyl)-1-piperidinyl]propyl} -2(3H)benzothiazolone; mp. 83° C.

Example XLVIII

A mixture of 7.24 parts of 1-(3-bromopropyl)-5-chloro-1,3-dihydro-2H-benzimidazol-2-one, 6.27 parts of 4-[2-(4-fluorophenyl)-1,3-dioxolan-2yl]piperidine, 3 parts of sodium carbonate and 180 parts of methylbenzene is stirred and refluxed overnight. The reaction mixture is filtered over hyflo while still boiling, and the filtrate is evaporated. The residue is boiled in 280 parts of 2,2'-oxybispropane. While stirring, the whole is allowed to cool to room temperature. The precipitated product is filtered off and dried in vacuo at 50° C, yielding 8 parts (69.6%) of 5-chloro-1-[3-{4-[2-(4-fluorophenyl)-1,3-dioxolan-2yl]-1-piperidinyl}propyl]-1,3-dihydro-2H-benzimidazol-2one; mp. 154.6° C.

Example IL

The products obtained in base form in the foregoing examples are treated with ethanolic hydrochloride in the standard manner to produce the corresponding hydrochloric acid addition salts. In turn, the latter, when treated with alkali (e.g. aqueous sodium hydroxide) yield the products in base form.

We claim:

1. A chemical compound selected from the group consisting of a piperidine derivative having the formula:

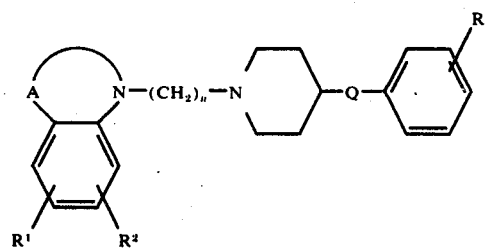

and the pharmaceutically acceptable acid addition salts thereof, wherein:

R is a member selected from the group consisting of hydrogen and halo;

$R^1$ and $R^2$ are each independently selected from the group consisting of hydrogen, halo, lower alkyl and trifluoromethyl;

n is an integer of from 2 to 4 inclusive;

Q is a member selected from the group consisting of

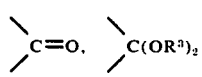 and

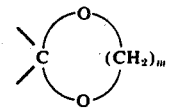

wherein $R^3$ is lower alkyl and m is an integer of from 2 to 3 inclusive; and

A is a bivalent radical selected from the group consisting of

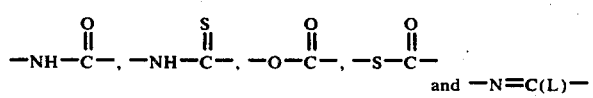

wherein L is selected from the group consisting of hydrogen, lower alkylthio, cyclohexyl and phenylmethyl, said bivalent radical being attached to the benzene nucleus by its heteroatom.

2. A chemical compound selected from the group consisting of 5-chloro-1-{3-[4-(4-fluorobenzoyl)-1-piperidinyl]propyl}-1,3-dihydro2H-benzimidazol-2-one and the pharmaceutically acceptable acid addition salts thereof.

3. A chemical compound selected from the group consisting of 1-{3-[4-(4-fluorobenzoyl)-1-piperidinyl]-propyl}-1,3-dihydro-5-methyl-2H-benzimidazol-2-one and the pharmaceutically acceptable acid addition salts thereof.

4. A chemical compound selected from the group consisting of 1-{3-[4-(4-fluorobenzoyl)-1-piperidinyl]-propyl}-1,3-dihydro-5,6-dimethyl-2H-benzimidazol-2-one and the pharmaceutically acceptable acid addition salts thereof.

5. A chemical compound selected from the group consisting of 1-[3-(2,3-dihydro-2-thioxo-1H-benzimidazol-1-yl)propyl]-4-piperidinyl (4-fluorophenyl)-methanone and the pharmaceutically acceptable acid addition salts thereof.

6. A chemical compound having the formula

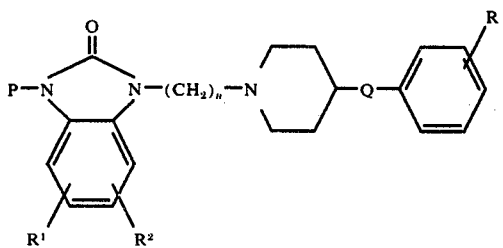

wherein:

R is a member selected from the group consisting of hydrogen and halo;

$R^1$ and $R^2$ are each independently selected from the group consisting of hydrogen, halo, lower alkyl and trifluoromethyl;

n is an integer of from 2 to 4 inclusive;

Q is a member selected from the group consisting of

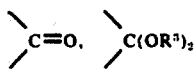

and

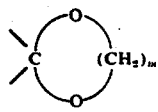

wherein $R^3$ is lower alkyl and $m$ is an integer of from 2 to 3 inclusive; and P is a member selected from the group consisting of lower alkyloxycarbonyl and a substituted ethenyl radical having the formula:

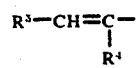

wherein $R^4$ is lower alkyl and $R^5$ is selected from the group consisting of hydrogen, lower alkyl and phenyl.

7. A chemical compound having the formula:

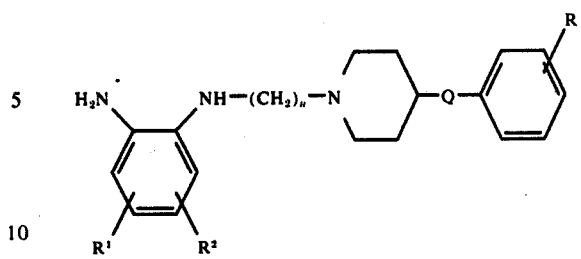

wherein:

R is a member selected from the group consisting of hydrogen and halo;

$R^1$ and $R^2$ are each independently selected from the group consisting of hydrogen, halo, lower alkyl and trifluoromethyl;

$n$ is an integer of from 2 to 4 inclusive; and

Q is a member selected from the group consisting of

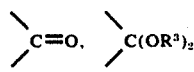

and

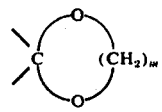

wherein $R^3$ is lower alkyl and $m$ is an integer of from 2 to 3 inclusive.

* * * * *

UNITED STATES PATENT AND TRADEMARK OFFICE
CERTIFICATE OF CORRECTION

PATENT NO. : 4,035,369

DATED : July 12, 1977

INVENTOR(S) : Jan Vandenberk, Ludo E. J. Kennis, Marcel J.M.C. Van Der Aa, Albert H. Th. Van Heertum It is certified that error appears in the above-identified patent and that said Letters Patent are hereby corrected as shown below:

At Column 7, Line 6, "if" should be -- it --.

At Column 11, Line 57, diagram "nitro-to-amine reduction →" should be -- nitro-to-amine reduction → (V) --.

At Column 14, Line 28, " LED (TRY) in mg/kg S.C.
0.08
5
2.5
0.31
5 " should be --
0.08
5
2.5
0.31
5 --.

UNITED STATES PATENT AND TRADEMARK OFFICE
CERTIFICATE OF CORRECTION

PATENT NO. : 4,035,369

DATED : July 12, 1977

INVENTOR(S) : Jan Vandenberk, Ludo E. J. Kennis, Marcel J.M.C. Van Der Aa, Albert H. Th. Van Heertum It is certified that error appears in the above-identified patent and that said Letters Patent are hereby corrected as shown below:

Column 14, 8th column in Table I:

| "LED (NOR) in mg/kg S.C. | should be |
|---|---|
| 2.5 | 2.5 |
| 2.5 | 2.5 |
| 5 | 5 |
| 5 | 5 |
| 2.5 | 2.5 |
| >10 | >10 |
| 1.25 | 1.25 |
| >10 | 10 |
| 5 | 5 |
| 0.31 | 0.31 |
| 5 | 5 |
| 10 | 10 |

At Column 19, Line 61, "5-chloro-2-(2-" should be -- 5-chloro-1-(2- --.

Signed and Sealed this

Sixth Day of February 1979

[SEAL]

Attest:

RUTH C. MASON
Attesting Officer

DONALD W. BANNER
Commissioner of Patents and Trademarks